United States Patent
Botta, Jr.

(10) Patent No.: US 12,383,731 B2
(45) Date of Patent: *Aug. 12, 2025

(54) AORTOPULMONARY ELECTRICAL STIMULATOR-PRESSURE TRANSDUCER

(71) Applicant: LIFE CHANGING MEDICAL TECHNOLOGIES, INC., Lake Mary, FL (US)

(72) Inventor: Donald Murrill Botta, Jr., Maitland, FL (US)

(73) Assignee: LIFE CHANGING MEDICAL TECHNOLOGIES, INC., Lake Mary, FL (US)

( * ) Notice: Subject to any disclaimer, the term of this patent is extended or adjusted under 35 U.S.C. 154(b) by 397 days.

This patent is subject to a terminal disclaimer.

(21) Appl. No.: 17/877,537

(22) Filed: Jul. 29, 2022

(65) Prior Publication Data

US 2022/0362541 A1 Nov. 17, 2022

Related U.S. Application Data

(60) Continuation-in-part of application No. 16/725,437, filed on Dec. 23, 2019, now Pat. No. 11,420,044, which is a division of application No. 15/646,735, filed on Jul. 11, 2017, now Pat. No. 10,589,084.

(60) Provisional application No. 62/344,923, filed on Jun. 2, 2016.

(51) Int. Cl.
| | | |
|---|---|---|
| *A61N 1/05* | (2006.01) | |
| *A61N 1/36* | (2006.01) | |
| *A61N 1/362* | (2006.01) | |
| *A61N 1/365* | (2006.01) | |
| *A61N 1/368* | (2006.01) | |

(52) U.S. Cl.
CPC ............ *A61N 1/05* (2013.01); *A61N 1/36114* (2013.01); *A61N 1/36139* (2013.01); *A61N 1/3622* (2013.01); *A61N 1/365* (2013.01); *A61N 1/3627* (2013.01); *A61N 1/36564* (2013.01); *A61N 1/368* (2013.01)

(58) Field of Classification Search
None
See application file for complete search history.

(56) References Cited

U.S. PATENT DOCUMENTS

| | | | |
|---|---|---|---|
| 4,536,893 A | * | 8/1985 | Parravicini ......... A61M 60/289 601/153 |
| 8,417,354 B2 | | 4/2013 | Zhang et al. |
| 2004/0230090 A1 | | 11/2004 | Hegde et al. |
| 2005/0149131 A1 | | 7/2005 | Libbus et al. |
| 2007/0299496 A1 | | 12/2007 | Podmore et al. |
| 2010/0023088 A1 | | 1/2010 | Stack et al. |
| 2010/0174336 A1 | | 7/2010 | Stein |
| 2010/0179374 A1 | * | 7/2010 | Stephens ............. A61M 60/538 600/16 |
| 2012/0271334 A1 | * | 10/2012 | Pless ................ A61B 17/22012 606/169 |

(Continued)

*Primary Examiner* — Erica S Lee
(74) *Attorney, Agent, or Firm* — Erica M. Cipparone; Wolter VanDyke Davis PLLC

(57) ABSTRACT

In an embodiment herein, an aortopulmonary stimulation method is provided including positioning at least one aortic electrode in or near the aorta, and using the at least one aortic electrode, to deliver stimulation to the aorta to decrease aortic after load.

18 Claims, 4 Drawing Sheets

(56) References Cited

U.S. PATENT DOCUMENTS

2012/0330092 A1* 12/2012 Shiose .................. A61N 1/056
                                                            600/18
2021/0085974 A1*  3/2021 Bouton ................ A61B 5/4836

* cited by examiner

AORTOPULMONARY ELECTRICAL STIMULATOR-PRESSURE TRANSDUCER

CROSS-REFERENCE TO RELATED APPLICATIONS

The present application is a continuation in part of and claims priority to U.S. Pat. No. 11,420,044, which is a divisional of application Ser. No. 15/646,735 filed Jul. 11, 2017 now U.S. Pat. No. 10,589,084 issued on Mar. 17, 2020, which claims priority to U.S. Provisional 62/344,923 filed Jun. 2, 2016. All patent and literature references cited in the present specification are hereby incorporated by reference in their entirety.

BACKGROUND

The degree of tension or stress on a heart muscle fiber as it contracts is termed the after load. Because pressure within the ventricles rises rapidly from a diastolic to a systolic value as blood is pumped out into the aorta and pulmonary arteries, the part of the ventricle that first contracts due to an excitatory stimulation pulse does so against a lower after load than does a part of the ventricle contracting later. Therefore, after load is the end load against which the heart contracts to eject blood. Many factors may influence the after load, one of which is the aortic pressure the left ventricular muscle must overcome to eject blood. A higher aortic/pulmonary pressure increases the after load on the left/right ventricle, respectively. The tension on the muscle fibers in the heart wall is the pressure within the ventricle multiplied by the volume within the ventricle divided by the wall thickness according to Laplace's law. This ratio is another factor used in determining the after load. By applying pressure on certain portions of the heart, after load can be greatly reduced or eliminated.

Prior art devices which attempt to address the aforementioned problems include pump-devices which surround certain portions of the heart to stimulate the portions. Other prior art devices include components that cross the pulmonic and tricuspid valves in order to stimulate the pulmonary artery.

Some other methods of attempting to modulate after load may include an extra-aortic balloon pump enabled to encircle the ascending aorta. This requires dissecting the aorta free from the pulmonary artery, which it abuts.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION OF THE DRAWINGS

Figure 1:
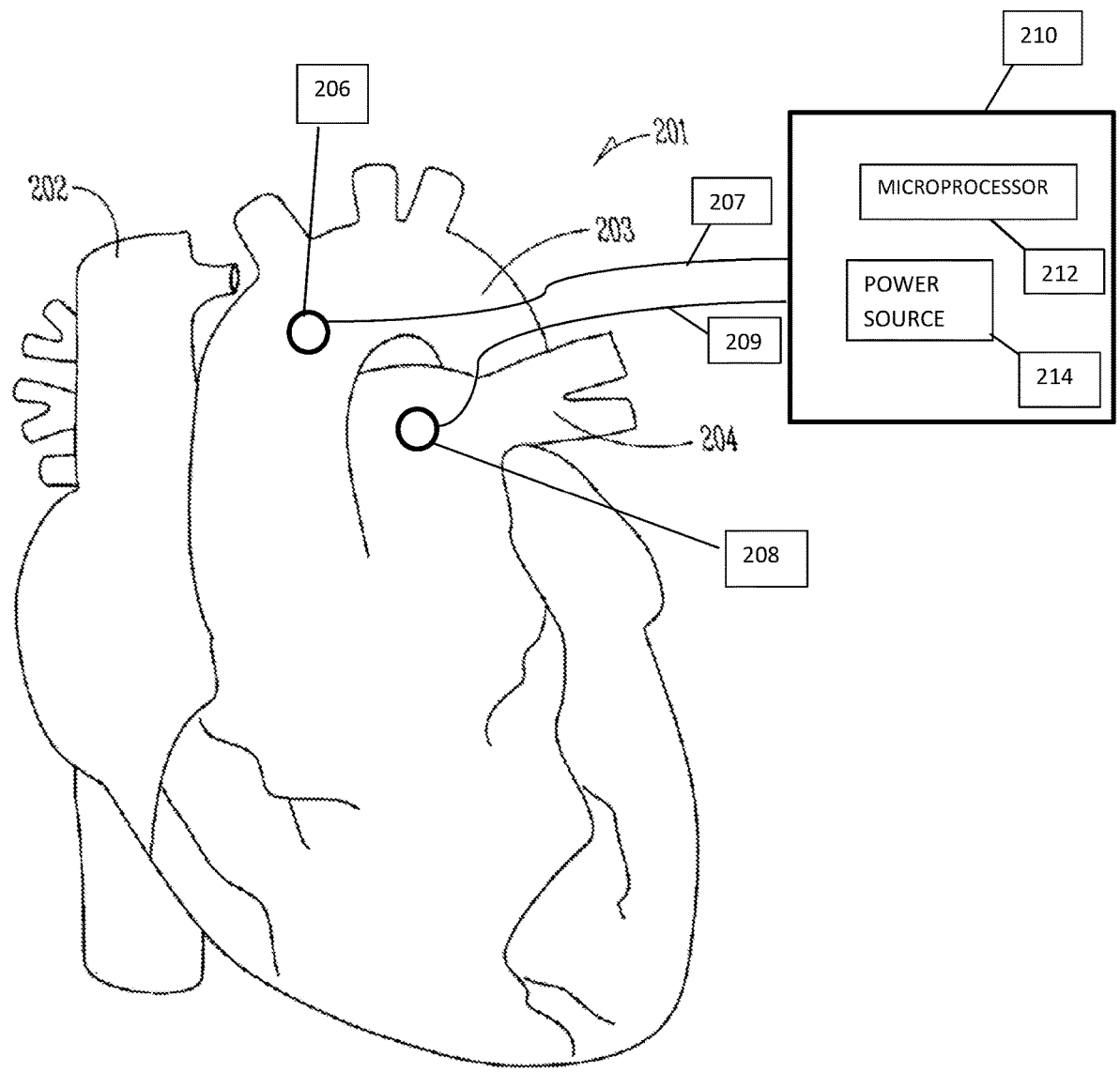
FIG. 1 provides a view of an embodiment of the placement of the device on a heart, in one example.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

The inventor has identified a condition of ambulatory heart failure treatment is after load reduction. Issues with after load often appear in cardiac surgery procedures. In order to remedy and/or prevent issues associated with these procedures, such as after load, the inventor has identified a novel method that induces beneficial neuro endocrine changes in a subject by pressure-induced activation of aortic baroreceptors.

The inventor has discovered that by stimulating the aorta and pulmonary artery with electrodes or otherwise as described herein, the pulmonary and aortic after load may be decreased in a measurable and adjustable manner. This way the effects of the stimulation will be measurable, and any adverse effects may be avoided. Methods currently used in the art to attempt to decrease afterload include IV medications, which result in substantial side effects. For example, side effects include an increase in myocardial oxygen demand. Other medications including nitroglycerin and nitride also result in damaging side effects when used. The inventive methods described herein would eliminate the need for the very costly intravenous drips currently used perioperatively during heart surgery procedures.

To eliminate the risks of dissecting between the aorta and the pulmonary artery, the inventor has discovered that both the aorta and the pulmonary artery may be encircled through the transverse pericardial sinus, taking advantage of a natural space and eliminating any risks associated with dissecting between the aorta and pulmonary artery.

Various embodiments described herein relate to a method. Other embodiments relate to a device. According to the various electrode embodiments described, at least one electrode used and is positioned in or on the aorta. Stimulation is applied using the at least one electrode. In other electrode embodiments, at least one electrode is positioned in or on the aorta and another electrode is positioned in or on a pulmonary artery. Stimulation is applied using at least one of the electrodes. Stimulation may be applied using both electrodes, and may be applied either simultaneously or one at a time. The stimulation may be varied in strength, duration, and sequence. The stimulation may be controlled by way of a control unit as described herein.

Many of the benefits of this device are achieved by activating baroreceptors. A baroreceptor includes any sensor of pressure changes, such as sensory nerve endings in the wall of the auricles of the heart, cardiac fat pads, vena cava, aortic arch and carotid sinus, that is sensitive to stretching of the wall resulting from increased pressure from within, and that functions as the receptor of the central reflex mechanism that tends to reduce that pressure. Additionally, a baroreceptor includes afferent nerve trunks, such as the vagus, aortic and carotid nerves, leading from the sensory nerve endings. Stimulating baroreceptors inhibits sympathetic nerve activity (stimulates the parasympathetic nervous system) and reduces systemic arterial pressure by decreasing peripheral vascular resistance and cardiac contractility. Some embodiments described herein stimulate baroreceptor sites in the pulmonary artery and/or in the aorta. Consequently, in another embodiment, using electrical stimulation to activate the baroreceptors may be accomplished with or without a pump. In order to monitor the effectiveness of the baroreceptor response, transducing the pressure in the vessels would be advantageous. Consequently, in an embodiment, the inventor has discovered an aortopulmonary electrical stimulator and/or pressure transducer array to achieve the abovementioned functions. The device may be minimally invasive, in an embodiment. The device may be used with minimal incisions.

One embodiment may include a transient array including leads configured to pass through a chest wall and associate with a control unit external to the subject. The control unit may be used to activate and/or inactivate the device, as well as to control the functions and features of the device as will be described in greater detail herein. The control unit may include stimulator circuitry, which may include modules to initiate or generate electrical pulses for delivery to the electrodes. The stimulator circuitry may be a component of the microprocessor. The microprocessor may be used to vary the amplitude of the stimulation pulse, the frequency of the pulse, the burst frequency, or the duty cycle of the pulse and the wave morphology of the pulse.

In one particular, non-limiting embodiment, the array and/or the leads may be disposable. In an embodiment, the leads may be removable from the subject perioperatively. The leads described herein may be percutaneously placed, in another non-limiting embodiment. In an embodiment, proximal and distal arrays surrounding the aorta and pulmonary arteries in the transverse pericardial sinus may be used. Tape-like component may be used to insulate the components of the device from surrounding structures, in a non-limiting embodiment.

Another embodiment may include a device including an implanted control unit which may be implanted into the body of the subject connecting to the leads of the device. In one non-limiting embodiment, the control unit may be implantable in a sub-pectoral location in the subject.

Non-limiting embodiments herein include an array which may include an array of output electrodes organized such that the aorta and the pulmonary artery may be individually stimulated. The arrays may be gated to provide various levels of stimulation to the aortic and pulmonary arteries as needed.

In an embodiment, strain gauges or other measurement devices know to those skilled in the art may be used to measure aortic and pulmonary artery pressures.

In another embodiment, additional cardiac leads may be added for biventricular pacing or defibrillator. The control unit may include wired or wireless connectivity for the communication of information and data to and from the control unit. in a non-limiting example, Bluetooth wireless technology may be employed.

The terms "subject" or "patient" may be used interchangeably herein. The terms include any animal or human subject.

Various embodiments of the present subject matter relate to a lead. Various lead embodiments comprise a lead body including a first portion, and at least a first branch. Other embodiments include a lead body including a first portion and at least a first branch and a second branch. The first portion has an end adapted to connect to an implantable medical device. The first branch may be connectable to either one of an aorta or a right or left pulmonary artery. The second branch may be connected to the first portion at a bifurcated region, in one non-limiting embodiment. The first branch may include a distal end adapted to be placed on or around the aorta, or fed into the aorta to securely position at least one electrode on or within the aorta. The second branch includes a distal end adapted to be placed onto or around or fed into a pulmonary artery to securely position at least one electrode on or within the pulmonary artery.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used or in another lead.

In one embodiment, a method for placing an electrode sleeve array comprising a sleeve body having a first end and a second end, and two or more electrodes, into a patient is provided. The method includes inserting a first end of a sleeve body around an aorta and pulmonary trunk through a transverse pericardial sinus, and affixing the first end of the sleeve body to a second end of the sleeve body with a fastener, such that the sleeve body encircles the aorta and the pulmonary artery.

In another embodiment, a method including positioning an aortic electrode in or near the aorta; and using the aortic electrode, to deliver stimulation to the aorta to decrease aortic after load is provided. In another non-limiting embodiment, the method may include positioning a pulmonary artery electrode in or near the pulmonary artery and using the pulmonary artery electrode to deliver stimulation to the pulmonary artery to decrease pulmonary artery after load.

In yet another embodiment, an aortopulmonary stimulation device is provided. The device includes an electrode sleeve array comprising a sleeve body, and two or more electrodes, the sleeve body comprising a first end and a second end for placement around the aorta and the pulmonary artery, in one embodiment, wherein upon placement of the sleeve array, at least a first electrode contacts the aorta, and at least a second electrode contacts the pulmonary artery. The device includes one or more leads connecting the electrode sleeve array to a control unit, the control unit for providing electrical stimulation to the electrode sleeve array, wherein upon initiation of electrical stimulation to the electrode sleeve array, the two or more electrodes deliver differential stimulation to the aorta and/or the pulmonary artery. In an alternative embodiment the sleeve body may be placed around the aorta or the pulmonary artery. In yet another embodiment, a first sleeve array may be placed around the aorta, and a second sleeve array may be placed around the pulmonary artery. In the aforementioned embodiments, the control unit of the device may further include a receptacle comprising a slave cable that may be attached to an intensive care unit (ICU) cardiac monitor. The control unit may receive inputs from the at least a first and second electrode, or electrode sleeve array. The control unit may deliver an output to another device. The output may include, in part, data received from the inputs from the electrode sleeve array. The control unit may include software for receiving and interpreting the inputs received from the electrode sleeve array, for example, to allow for gating of the device output based on the EKG inputs.

In at least another embodiment, the device may include a fully implanted device comprising a receptacle for pacemaker leads, or a plurality of receptacles for a plurality of leads. The fully implanted device may include software to read EKG inputs received from the sensors, and to gate the aortic and pulmonary baroreceptor output delivery. The device may further provide cardiac pacing through one or more leads.

The device, in some non-limiting embodiments, may include one or more defibrillator leads. The device may further include a power source for delivering defibrillation via the defibrillator leads.

The aortopulmonary stimulation device, in some embodiments, may be communicatingly connected to an external device, such as a smart device in some non-limiting embodiments, for receiving data from the device. The smart device may be used to control the aortopulmonary stimulation device and to provide input to and receive outputs from the aortopulmonary stimulation device. In some embodiments the strength, frequency, and other details of the electrical stimulation via the electrode sleeve array may be controlled by way of the smart device or other external device.

Turning to the drawings, FIG. 1 provides a side view of a heart 201 including a superior vena cava 202, aorta 203 and pulmonary artery 204. A first electrode 206 may be placed in or on the aorta 203, and a first lead 207 connecting the first electrode to a control unit 210. A second electrode 208 may be placed in or on the pulmonary artery 204 and a second lead 209 connecting the second electrode 208 to the control unit 210. The control unit 210 may include a microprocessor 212 and a power source 214. The control unit 210 may be used to initiate the electrodes 206, 208 to stimulate the aorta 203 and the pulmonary artery 204. Both the aorta 203 and the pulmonary artery 204 may be simultaneously stimulated or may be stimulated at different times. The electrodes 206, 208 may be stimulated independently of one another to differentially stimulate the aorta and pulmonary artery.

Figure 2:
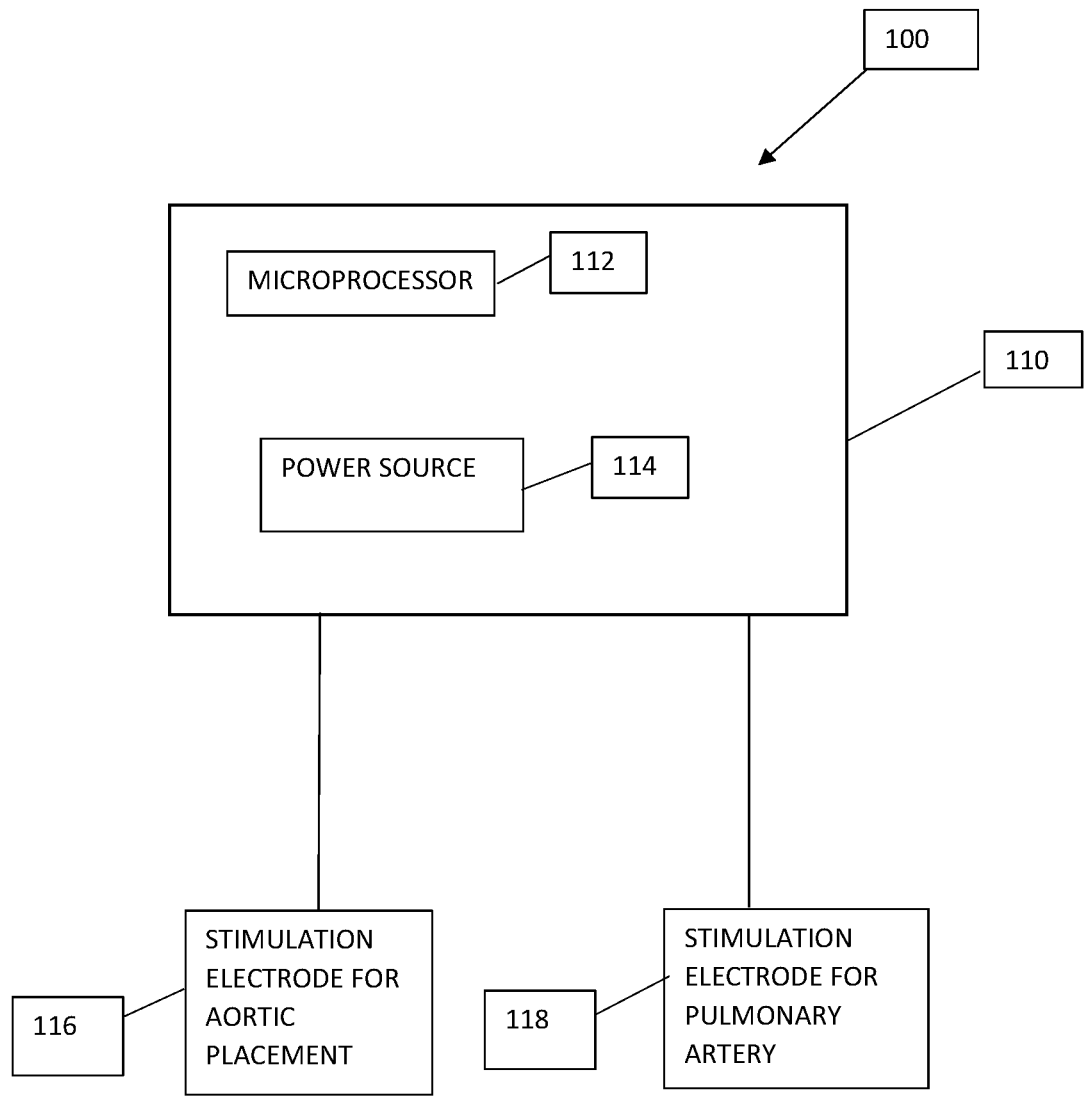
FIG. 2 provides a schematic of an aortopulmonary electrical stimulation embodiment.

FIG. 2 provides a schematic view of the device 100, wherein a control unit 110 including a microprocessor 112, and a power source 114 is provided. A first electrode for aortic placement 116 is associated with the control unit 110, and a second electrode, for stimulation of the pulmonary artery 118 is associated with the control unit 110.

Figure 3:
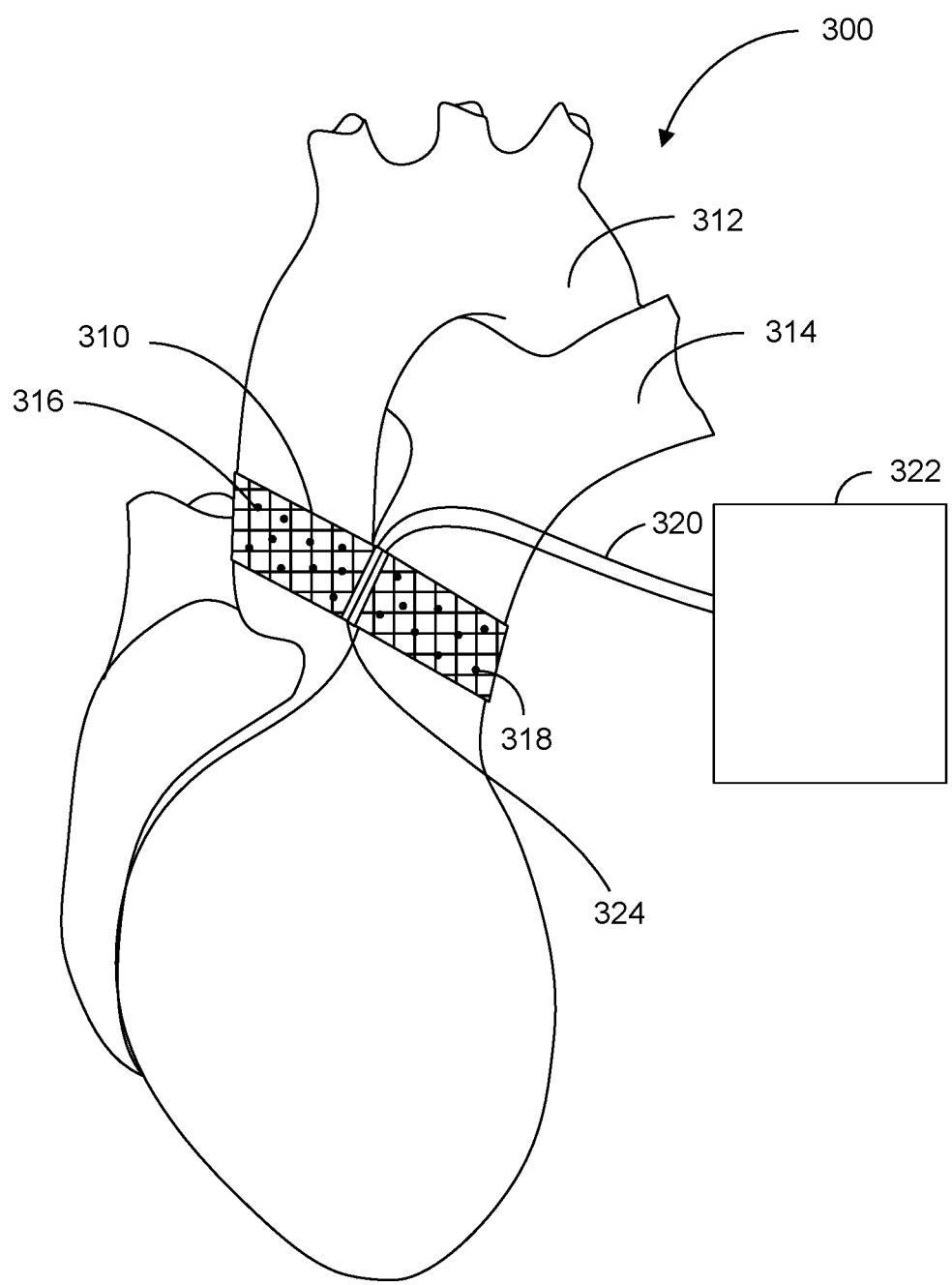
FIG. 3 provides a non-limiting embodiment of an aortopulmonary electrical stimulation device including a sleeve array.

FIG. 3 provides a side view of a device embodiment 300, wherein a sleeve array 310 is placed on the aorta 312 and the pulmonary artery 314. When the sleeve array 310 is placed on the aorta 312 and the pulmonary artery 314, at least a first electrode 316 contacts the aorta 312, and at least a second electrode 318 contacts the pulmonary artery 314. Electrical simulation is delivered to the aorta 312 and the pulmonary artery 314 by way of electrical leads 320, which are connected to an electrical pulse generator, i.e., a control unit 322. A fastening device 324 may be used to affix the sleeve array 310 to the aorta 312 and pulmonary artery 314.

Figure 4:
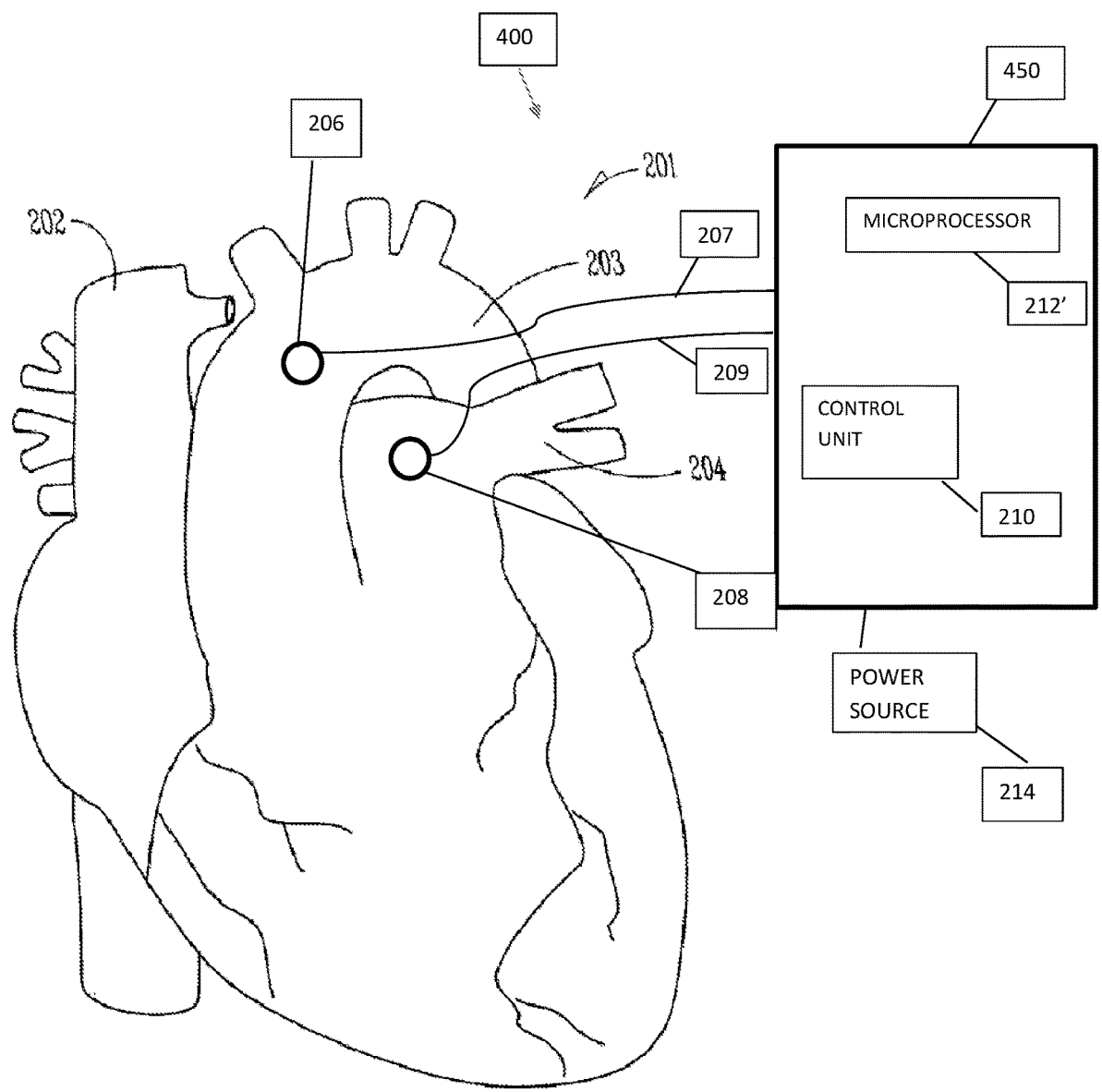
FIG. 4 provides a view of another embodiment of the device on a heart.

FIG. 4 provides a side view of an embodiment of an aortopulmonary stimulation device 400 associated with a heart 201. The heart 201 is shown including its superior vena cava 202, aorta 203 and pulmonary artery 204. A first electrode 206 of the device 400 may be placed in or on the aorta 203, and a first lead 207 connecting the first electrode to a smart device 450 comprising a control unit 210. A second electrode 208 may be placed in or on the pulmonary artery 204 and a second lead 209 connecting the second electrode 208 to the smart device 450. The smart device 450 may include a microprocessor 212 and a power source 214, in addition to the control unit 210. An external device may be used in place of a smart device 450, and need not include smart features. In this embodiment, the external device includes the control unit 210 and may be associated with a power source 214. The external device may be used to receive inputs from the aortopulmonary stimulation device 400 and may provide outputs to a user or to another device or system.

The control unit 210 may be used to initiate the electrodes 206, 208 to stimulate the aorta 203 and the pulmonary artery 204 via the smart device 450 or via another connected external device. Both the aorta 203 and the pulmonary artery 204 may be simultaneously stimulated or may be stimulated at different times. Variations to the stimulation speed, intensity, duration, and other details may be provided via the smart device 450. The electrodes 206, 208 may be stimulated independently of one another to differentially stimulate the aorta and pulmonary artery, in one example.

The device may further include one or more pacemaker and/or defibrillator leads associated therewith. These leads may be connected to and controlled by the controller, the smart device, or the external device.

In one embodiment, a method including positioning at least one aortic electrode in or near the aorta, and using the at least one aortic electrode, to deliver stimulation to the aorta to decrease aortic after load is provided. In a further embodiment, the method includes positioning at least one pulmonary artery electrode in or near the pulmonary artery and using the at least one pulmonary artery electrode to deliver stimulation to the pulmonary artery to decrease pulmonary artery after load. In one example baroreceptors are stimulated. In another embodiment, the method includes delivering a variable level of stimulation to the aorta. In yet another embodiment, the method includes delivering a variable level of stimulation to the pulmonary artery. In further embodiment, the method may include a device comprising one or more strain gauges configured to measure the aortic and/or pulmonary artery pressure. In some examples, based on the pressure detected, a variable stimulation of the aorta and/or pulmonary artery is executed.

In another embodiment, a first electrode sleeve array comprising a sleeve body and at least one aortic electrode may be provided, wherein a method of reducing after load includes inserting a first end of the sleeve body around the aorta and pulmonary trunk through a transverse pericardial sinus, and affixing the first end of the sleeve body to a second end of the sleeve body, such that the sleeve body encircles the aorta and the pulmonary artery.

The method may further include wherein the sleeve body of the device further comprises a fastener, and the method includes affixing the first end of the sleeve body is to the second end of the sleeve body via the fastener In yet another non-limiting embodiment, a method for placing an electrode sleeve array comprising a sleeve body having a first end and a second end, and two or more electrodes, into a patient, includes inserting a first end of a sleeve body around an aorta and pulmonary trunk through a transverse pericardial sinus, and affixing the first end of the sleeve body to a second end of the sleeve body with a fastener, such that the sleeve body encircles the aorta and/or the pulmonary artery.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A method, comprising:
a first electrode sleeve array comprising a sleeve body and at least one aortic electrode, the method comprising inserting a first end of the sleeve body around the aorta and pulmonary trunk through a transverse pericardial sinus to position the at least one aortic electrode in or near the aorta, and affixing the first end of the sleeve body to a second end of the sleeve body, such that the sleeve body encircles the aorta and the pulmonary artery;
initiating an electrical stimulation via a smart device communicatingly connected to the first electrode sleeve array to deliver electrical stimulation to the array;
wherein an electrical stimulation delivered to the first electrode sleeve array causes electrical stimulation via the at least one aortic electrode to the aorta to decrease aortic after load.

2. The method of claim 1, further comprising:
wherein the first electrode sleeve array comprises at least one pulmonary artery electrode, and wherein at the inserting step, the at least one pulmonary artery electrode is positioned in or near the pulmonary artery, such that the at least one pulmonary artery electrode delivers stimulation to the pulmonary artery to decrease pulmonary artery after load.

3. The method of claim 2, comprising delivering a variable level of stimulation to the pulmonary artery.

4. The method of claim 2, further comprising one or more strain gauges configured to measure the pulmonary artery pressure.

5. The method of claim 4, wherein based on the pulmonary artery pressure detected, a variable stimulation of the pulmonary artery is executed.

6. The method of claim 1, wherein baroreceptors are stimulated.

7. The method of claim 1, comprising delivering a variable level of stimulation to the aorta.

8. The method of claim 1, further comprising one or more strain gauges configured to measure the aortic pressure.

9. The method of claim 8, wherein based on the aortic pressure detected, a variable stimulation of the aorta is executed.

10. An aortopulmonary stimulation device, comprising:
a first electrode sleeve array comprising a sleeve body and at least one aortic electrode;
the sleeve body comprises a first end and a second end, the sleeve body configured for inserting around the aorta and pulmonary trunk through a transverse pericardial sinus to position the at least one aortic electrode in or near the aorta, said first end of the sleeve body configured for affixing to the second end of the sleeve body;
one or more leads associated with the electrode sleeve array for delivering electrical stimulation thereto;
a control unit for associating with the one or more leads for controlling the electrical stimulation;
wherein an electrical stimulation delivered to the first electrode sleeve array causes electrical stimulation via the at least one aortic electrode to the aorta to decrease aortic after load.

11. The device of claim 10, further comprising a pulmonary artery electrode in the electrode sleeve array, the pulmonary artery electrode configured for positioning in or near the pulmonary artery, such that the at least one pulmonary artery electrode delivers stimulation to the pulmonary artery to decrease pulmonary artery after load.

12. The device of claim 10, further comprising one or more strain gauges configured to measure the aortic pressure and/or the pulmonary artery pressure.

13. The device of claim 12, wherein based on the aortic or pulmonary artery pressure detected via the one or more strain gauges, a variable stimulation of the aorta and/or the pulmonary artery is executed.

14. The device of claim 10, wherein the sleeve body further comprises a fastener to affix the first end of the sleeve body to the second end of the sleeve body.

15. The device of claim 10, wherein a smart device is communicatingly connected to the device, said smart device for receiving input from the electrode sleeve array and for providing output to a user or another device.

16. The device of claim 15, wherein the smart device controls the electrical stimulation delivered to the electrode sleeve array.

17. The device of claim 10, further comprising one or more defibrillator leads configured for delivering defibrillation.

18. The device of claim 10, further comprising one or more pacemaker leads to provide baroreceptor output delivery or cardiac pacing, or a combination thereof.

* * * * *